US010391087B2

(12) United States Patent
Cortes Borrego

(10) Patent No.: US 10,391,087 B2
(45) Date of Patent: Aug. 27, 2019

(54) COMBINATION OF OXYMETAZOLINE AND IPRATROPIUM IN TOPICAL NASAL APPLICATION FOR THE TREATMENT OF A COUGH

(71) Applicant: Pablo Cortes Borrego, Mexico City (MX)

(72) Inventor: Pablo Cortes Borrego, Mexico City (MX)

( * ) Notice: Subject to any disclaimer, the term of this patent is extended or adjusted under 35 U.S.C. 154(b) by 0 days.

(21) Appl. No.: 15/778,067

(22) PCT Filed: Mar. 17, 2016

(86) PCT No.: PCT/MX2016/000028
§ 371 (c)(1),
(2) Date: May 22, 2018

(87) PCT Pub. No.: WO2017/095210
PCT Pub. Date: Jun. 8, 2017

(65) Prior Publication Data
US 2018/0344722 A1 Dec. 6, 2018

(30) Foreign Application Priority Data
Dec. 2, 2015 (MX) .................... MX/a/2015/016549

(51) Int. Cl.
| *A61K 31/46* | (2006.01) |
| *A61K 9/08* | (2006.01) |
| *A61K 9/00* | (2006.01) |
| *A61P 11/14* | (2006.01) |
| *A61K 31/4174* | (2006.01) |
| *A61K 47/02* | (2006.01) |
| *A61K 47/10* | (2017.01) |
| *A61K 47/18* | (2017.01) |

(52) U.S. Cl.
CPC ............ *A61K 31/46* (2013.01); *A61K 9/0043* (2013.01); *A61K 9/08* (2013.01); *A61K 31/4174* (2013.01); *A61P 11/14* (2018.01); *A61K 47/02* (2013.01); *A61K 47/10* (2013.01); *A61K 47/183* (2013.01); *A61K 47/186* (2013.01); *A61K 2300/00* (2013.01)

(58) Field of Classification Search
CPC ...... A61K 31/46; A61K 9/08; A61K 31/4147; A61P 11/14
USPC ........................................................ 514/304
See application file for complete search history.

(56) References Cited

U.S. PATENT DOCUMENTS

| 7,867,508 B1 * | 1/2011 | Smith | .................... A61K 45/06 424/434 |
| 2009/0238771 A1 * | 9/2009 | Berry | .................. A61K 9/0043 424/45 |

FOREIGN PATENT DOCUMENTS

| WO | 2003/024433 | 3/2003 |
| WO | 2014/158119 A1 | 10/2014 |

OTHER PUBLICATIONS

FDA Publication of Combivent Respimat inhalation, (2011). (Year: 2011).*
Madison et al. Expert Opion on Pharmacotherapy, (2003), 4(7), p. 1039-1048 (Year: 2003).*
Madison, J. M. et al.: "Pharmacotherapy of chronic cough in adults", Expert Opinion on Pharmacotherapy., vol. 4, No. 7, Jul. 2003 (Jul. 1, 2003), pp. 1039-1048., XP055388477, ISSN: 1465-6566.
Smyrnios, N. A. et al.: "Chronic cough with a history of excessive sputum production: The spectrum and frequency of causes, key components of the diagnostic evaluation, and outcome of specific therapy.", Chest., vol. 108, No. 4, Oct. 1995 (Oct. 1, 1995), pp. 991-997, XP055388617, ISSN: 0012-3692.
Turner, R. B. et al.: "Epidemiology, pathogenesis, and treatment of the common cold.", Annals of Allergy, Asthma & Immunology., vol. 78, No. 6, Jun. 1997 (Jun. 1, 1997), pp. 531-540., XP005466420, ISSN: 1081-1206.
Ghafouri, M. A. et al.: "Sputum changes associated with the use of ipratropium bromide.", Chest., vol. 86, No. 3, Sep. 1984 (Sep. 1, 1984), pp. 387-393., ISSN: 0012-3692.
Pitkäranta, A. et al.: "Combined intranasal ipratropium bromide and oxymetazoline in experimental rhinovirus infection.", American Journal of Rhinology., vol. 12, No. 2, Mar. 1998 (Mar. 1, 1998), pp. 125-129., ISSN: 1050-6586.

* cited by examiner

Primary Examiner — Yong L Chu
(74) Attorney, Agent, or Firm — Bay State IP, LLC

(57) ABSTRACT

The present invention is effective for the treatment and relief of cough produced by posterior nasal secretion, through the use of the combination of Oximetazoline and Ipratropium. The active agents enunciated in the combination of the present invention have been used and marketed separately with different uses to those of the present invention. The oxymetazoline to eliminate nasal secretion and congestion (obstruction), and ipratropium bromide is marketed for the purpose of dilating the bronchial tubes in asthmatic patients with chronic obstructive pulmonary disease, although experimentally it has also been used to decrease nasal secretion. Both active agents, together or separately have not been used so far as antitussives intranasally. The cough produced by the posterior nasal secretion, is the most frequent cause of cough in the human being of any age, the present invention is effective for the treatment and relief of said symptom.

8 Claims, 6 Drawing Sheets

SYMPTOMS DURING THE DAY

Please, CROSS the number you consider is the best reflecting how intense was your son's/daughter's cough during the day.

| No cough | Cough for one or two short periods | Cough for more than two short periods | Cough is frequent but NOT interfering with school or other activities | Cough is frequent and IT DOES interfere with school and other activities | He/She can not make most of his/her usual activities because of the cough |
|---|---|---|---|---|---|
| CROSS | CROSS | CROSS | CROSS | CROSS | CROSS |
| 0 | 1 | 2 | 3 | 4 | 5 |

How was the cough the during the day? (A DAY BEFORE CONSULT)
| 0 | 1 | 2 | 3 | 4 | 5 |

How was the cough the during the day? (TREATMENT DAY 1)
| 0 | 1 | 2 | 3 | 4 | 5 |

How was the cough the during the day? (TREATMENT DAY 2)
| 0 | 1 | 2 | 3 | 4 | 5 |

How was the cough the during the day? (TREATMENT DAY 3)
| 0 | 1 | 2 | 3 | 4 | 5 |

How was the cough the during the day? (TREATMENT DAY 4)
| 0 | 1 | 2 | 3 | 4 | 5 |

How was the cough the during the day? (TREATMENT DAY 5)
| 0 | 1 | 2 | 3 | 4 | 5 |

How was the cough the during the day? (DAY 6, WITH NO TRATMENT)
| 0 | 1 | 2 | 3 | 4 | 5 |

How was the cough the during the day? (DAY 7, WITH NO TREATMENT)
| 0 | 1 | 2 | 3 | 4 | 5 |

FIGURE 3

SYMPTOMS DURING THE NIGHT

Please, CROSS the number you consider is the best reflecting how intense your son's /daughter's cough was during the night.

| No cough | Cough waking up | Wakes up at night once or wakes up earlier because of the cough | Wakes up frequently because of the cough | Coughs frequently most of the night | Coughs all night without falling asleep |
|---|---|---|---|---|---|
| CROSS 0 | CROSS 1 | CROSS 2 | CROSS 3 | CROSS 4 | CROSS 5 |

How was the cough the _____ during the night? (A NIGHT BEFORE CONSULT)
| 0 | 1 | 2 | 3 | 4 | 5 |

How was the cough the _____ during the night? (TREATMENT NIGHT 1)
| 0 | 1 | 2 | 3 | 4 | 5 |

How was the cough the _____ during the night? (TREATMENT NIGHT 2)
| 0 | 1 | 2 | 3 | 4 | 5 |

How was the cough the _____ during the night? (TREATMENT NIGHT 3)
| 0 | 1 | 2 | 3 | 4 | 5 |

How was the cough the _____ during the night? (TREATMENT NIGHT 4)
| 0 | 1 | 2 | 3 | 4 | 5 |

How was the cough the _____ during the night? (TREATMENT NIGHT 5)
| 0 | 1 | 2 | 3 | 4 | 5 |

How was the cough the _____ during the night? (NIGHT 6, WITH NO TRATMENT)
| 0 | 1 | 2 | 3 | 4 | 5 |

How was the cough the _____ during the night? (NIGHT 7, WITH NO TRATMENT)
| 0 | 1 | 2 | 3 | 4 | 5 |

FIGURE 4

COMBINATION OF OXYMETAZOLINE AND IPRATROPIUM IN TOPICAL NASAL APPLICATION FOR THE TREATMENT OF A COUGH

CROSS REFERENCE TO RELATED APPLICATION

This application is for entry into the U.S. National Phase under § 371 for International Application No. PCT/MX2016/000028 having an international filing date of Mar. 17, 2016, and from which priority is claimed under all applicable sections of Title 35 of the United States Code including, but not limited to, Sections 120, 363, and 365(c), and which in turn claims priority under 35 USC 119 to Mexican Patent Application No. MX/a/2015/016549 filed on Dec. 2, 2015.

ABSTRACT

The invention is related with the use of the combination of oximetazoline and ipratropium, or each component separately administrated via intranasally for cough relief. The cough caused by posterior nasal secretion discharge.

BACKGROUND

Ipratropium, is a derivative of N-isopropil noratropine, with anticholinergic effects in the upper respiratory tract. The basic patent is U.S. Pat. No. 3,505,337. For symptomatic treatment of the rhinorrhea associated with perennial rhinitis, a nasal spray (Atrovent®) is available in the market.

Oxymetazoline is an imidazol-simpathetic vasoconstrictor preferably used locally intranasal to unblock nasal mucous membrane. The basic patent of oximetazoline is DE 1117588 (Merck® lliadin, metered dose aerosol, drops, pediatric aerosol) is available in the market. There is an aerosol containing Ipratropium and Xilometazoline, a similar molecule, available the market (Otrivin Com®) It has been described a combination of oxyrnetazoline or a derivative of its salt, with ipratropium or a derivative of its salt for the treatment of symptoms of common cold and/or rhinitis and related symptoms such as nasal congestion, sneezing and hypersecretion (WO 2014158119 A1) which is not actually in the market, with the following composition:

| Ingredients | Quantity |
| --- | --- |
| Ipratropium Bromide | 0.005%-0.5% weight/Volume(0.05 mg/ml-5 mgs/ml) |
| Oximetazoline hydrochloride | 0.005%-0.5% weight/Volume(0.05 mg/ml-5 mgs/ml) |
| EDTA disodium | 0.005%-0.1% weight/volumen |
| Glycerol | 0%-30.0% weight/volumen |
| Benzalconium Chlorate | 0%-0.02 weight/volumen |
| Buffer (pH adjust) | u.s. |
| Water | u.s. |

There is a previous patent number 247216 with International Publication WO 03/024433 A2 which comprises the combination of ipratropium bromide and Xilometazolina for symptoms associated with common cold based on nasal congestion, sneezing and hypersecretion, caused by viral infections, allergic or perennial rhinitis.

However, a preparation comprising oxymetazoline salt or derivative, in combination with ipratropium bromide salt or derivative, intranasally used, specifically for relief of cough caused by increased discharge runny nose, towards the retro-nasopharynx, or also called, postnasal drip syndrome has not been described and is not currently available in the market.

The oxymetazoline hydrochloride is a sympathetic agent that shrinks arterioles network within nasal mucosa producing long decongestive and antisecretor effects, therefore it has been used in common cold, to permeate nostrils and decrease rhinorrhea (synonym: catarrh, coryza, nasopharyngitis, cold or flu).

Oxymetazoline dilutions used 0.01 for babies of 6 months to two years of age, 0.25% for children aged 2 to 12 years old and 0.50% ai for children and adults aged 12 years or older.

Ipratropium Bromide is an anticolinergic agent that antagonizes the action of acetylcholine released by nerve endings. Nasal hypersecretion associated to common cold and other upper respiratory tract infections involves neurogenic reflexes with release of acetylcholine at the nasosinusal mucosa level. These reflexes are antagonized by atropine and ipratropium bromide (both are anticolinergic, with anti-acetylcholine effect). This has been proven by studies in which nasal fluid was measured in individuals with naturally acquired common cold[1-3].

At the present time, approaches to the use of oxymetazoline and Ipratropium, are:

For oxymetazoline hydrochloride, because its permeate effect of nose due to reduce congestion of the nasal mucosal superficial vessels (decongestant effect), with concomitant decrease volume occupied by these tissues (particularly the turbinate erectil tissue), increasing the nostrils light, which allows more space for air passage when they are blockade during a common cold, nasopharyngitis or allergic rhinitis. Due to this same vasoconstrictor effect also is decreased the nasal fluid production (since the distended vessels release liquid to nostrils (watery discharge of the common cold)[4-6].

Therefore, It is used to relieve nasal congestion and excess mucus fluid, not to alleviate cough.

For ipratropium bromide, it has been traditionally used as a bronchodilator in asthma and chronic obstructive pulmonary disease, being its main use by micronebulizator[7-9] or by oral metered dose inhaled aerosol. More recently it has been experimentally used to reduce nasal secretion[11,18].

BRIEF DESCRIPTION OF THE DRAWINGS

FIG. 3 illustrates a spreadsheet to evaluate a patient's symptoms during the day after administration of the composition.

FIG. 4 illustrates a spreadsheet to evaluate a patient's symptoms during the day after administration of the composition.

DETAILED DESCRIPTION OF THE INVENTION

Figure 1:
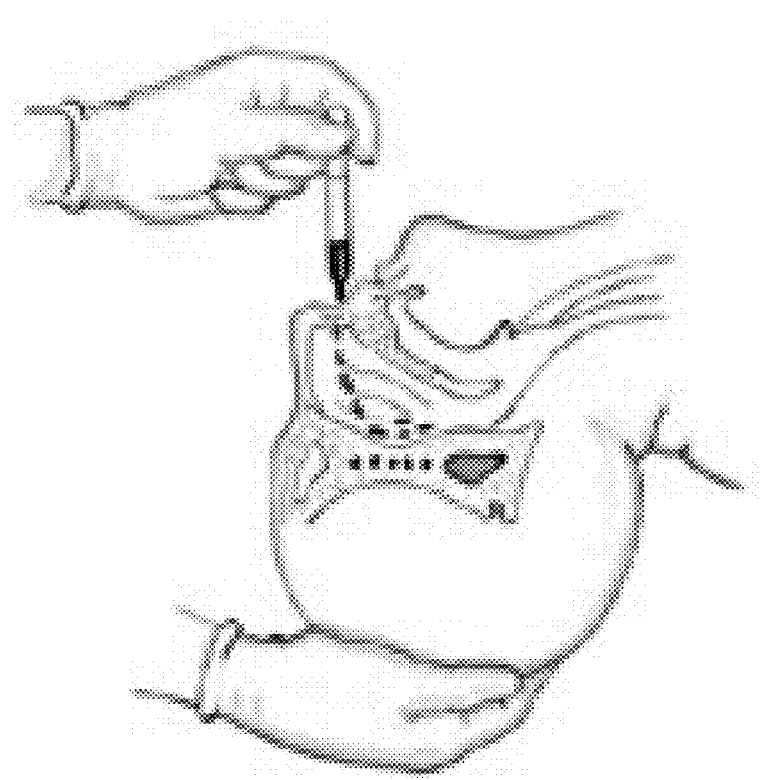
FIG. 1 illustrates how a composition is administered "intranasally" into both nostrils, with hyperextension of the neck, in order to allow drops go to depth nares by gravity.

The invention is designed for symptomatic treatment of cough due to post nasal drip syndrome using the combination: Ipratropium bromide and oxymetazoline hydrochloride (or each component separately) intranasal.

The term "symptomatic treatment of cough" refers to a medical and pharmacological intervention, which serves to reduce or eliminate cough, that is to say, as an antitussigen agent without necessarily act on the primary etiology of cough (for example, in viruses or bacterial infections, or in the immunologic disturbance which cause allergy), but yes on the consecuence of it, which very often is, postnasal drip syndrome, which directly causes cough.

The cough to which it refers is that produced mainly during viral rhinopharyngitis (the so-called "flu", "colds" or "common cold"), as well as those produced by bacterial infections such as rhinopharyngitis or bacterial rhinosinusitis, which may lengthen the course of cough Also the cough to which it refers, is one that tends to get worse predominantly during the nights and mornings. This is because in the dorsal decubitus position, secretion flows more easily, towards the human posterior nasopharyngeal part. Or, it is mobilized in the mornings, the secretion that has accumulated during the night.

The term "posterior drip syndrome" (SGNP) refers to the flow of secretion from the nasal and sinus mucosa, which is directed towards the back of the nose, by its natural drainages (meatus, osteomaetal complexes and the nose itself), which then drains through the posterior nasopharyngeal, oro-pharyngeal and hypopharyngeal walls. It is also referred to as Cough Syndrome due to Rhinosinusal Disease or CSRSD. Since they do not always show secretion data to produce cough[12].

The etiology of this syndrome is varied, however it is most frequently due to viral or bacterial infection (rhinopharyngitis, flu, infectious rhinitis, rhinosinusitis, etc.) but it can also be due to allergic reactions, or as a result of exposures to different irritants or physical changes of the environment on the mucosa of the upper respiratory tract.

The term Ipratropium or derivative of its salt, tries to relate to Ipratropium and one or more derivatives of its salt, pharmaceutically acceptable. A pharmaceutically acceptable salt of Ipratropium is selected from the group of ipratropium bromide, ipratropium chloride, ipratropium iodide, ipratropium fluoride, oxitropium bromide as well as other atropine derivatives such as tiotropium bromide and aclidinium bromide or the more selective cholinergic antagonists of $M_3$ receptors, darifenacin (UK-88.525) and retropate (UK-112.116).

The term oxymetazoline and salt thereof, tries to correlate with Oximetazoline or a pharmaceutically acceptable salt selected from Oxymetazoline hydrochloride, Oxymetazoline hydrobromide, Oximetazoline hidroxide, Oxymetazoline hydrofluoride, Oxymetazoline sulfate, Oxymetazoline nitrate, Oxymetazoline acetate, Oxymetazoline tartrate, Oxymetazoline fumarate. As well as chemically related substances like Xilometazoline, Nafazoline, phenylephrine, etc.

The term "pharmaceutically acceptable salts" denotes the meaning of essentially non-toxic substances from its administration to nasal mucosa, like: ethers, acetates, fumarates, hydrochlorides.

The term "intranasally" refers to the administration of the combination each of its components, drops or spray, instilled into both nostrils, with hyperextension of the neck, in order to allow drops go to depth nares by gravity (FIG. 1), by allowing a period not less than one minute, then inhale hard, covering the contralateral nostril and then conversely, covering the other nostril to repeat a forced inhalation. The concept is that the solution enters the backest part of the nose. However the combination can be administrated by spray, with head erected, directing the spray up and backward.

The present invention is the use of a combination of Ipratropium oxymetazoline wherein: Quantitative formula

| | |
|---|---|
| Oximetazoline hidrochlorhide | 50.0 mg - 25.0 mg - 10.0 mg |
| | Adult - Infant - Pediatric |
| Ipratropium bromide | 52.5 mg |
| Glycerine | 5000.0 mg |
| Monobasic potassium fosfate | 68.04 mg |
| Disodium EDTA (disodium etilendiamine-tetra-acetate) | 50.0 mg |
| Benzalconium Chloride | 10.0 mg |
| Sodium hydroxide Solution 0.1N | To adjust at pH 4.75 |
| Hydrochloric acid 0.1N | To adjust at pH 4.75 |
| Purified water u.s. | u.s. 100 ml | u.s. The sufficient to

A similar solution, with another different imidazoline derivative than oxymetazoline was used by Dr. Eccles[2] intranasally to reduce colds nasal obstruction, but not to treat cough. This combination consists of:

Xilometazoline (another derivative of imidazoline similar to oximetazoline) in different: 1, 0.5, 1.0 mg/mL combined with Ipratropium Bromide at a constant dilution 0.6 mgs/mL and glycerol, sodium edetate and hydrochloric acid to get a pH 4.5. In a dropper bottle 10 mL with each dose of 140 µL.

With respect to the previous art in relation to pre-existing cough drugs, literature persistently matches with that current drugs (antihistaminics, decongestants, antitussives, expectorants, bronchodilators, etc.) and other alternative remedies have not been superior than placebo to relief cough, in meta-analysis and reviews of randomized, double-blind, placebo-controlled studies[13,27]. This includes all over-the-counter drugs (also called self-prescription drugs) such as syrups, expectorants, etc. used to relieve cough from any cause.

So that with respect to the prior art, not an specific antitussive topical nasal are known, directed exclusively towards the most common cause of cough in human being it is, secretion discharge to the back of the nose flow through the oropharynx posterior wall, hypopharynx and larynx with stimulation of nerve endings[51,112].

Preferred embodiments of the invention are forms: drops, aerosol, pressurized metered dose aerosol, spray or microspray, spray, nasal breeze, nasal spray or by the Respimat™, nozzle Sterimar™, Genuair® devices or any other device to diffuse fluids intranasally.

Figure 2:
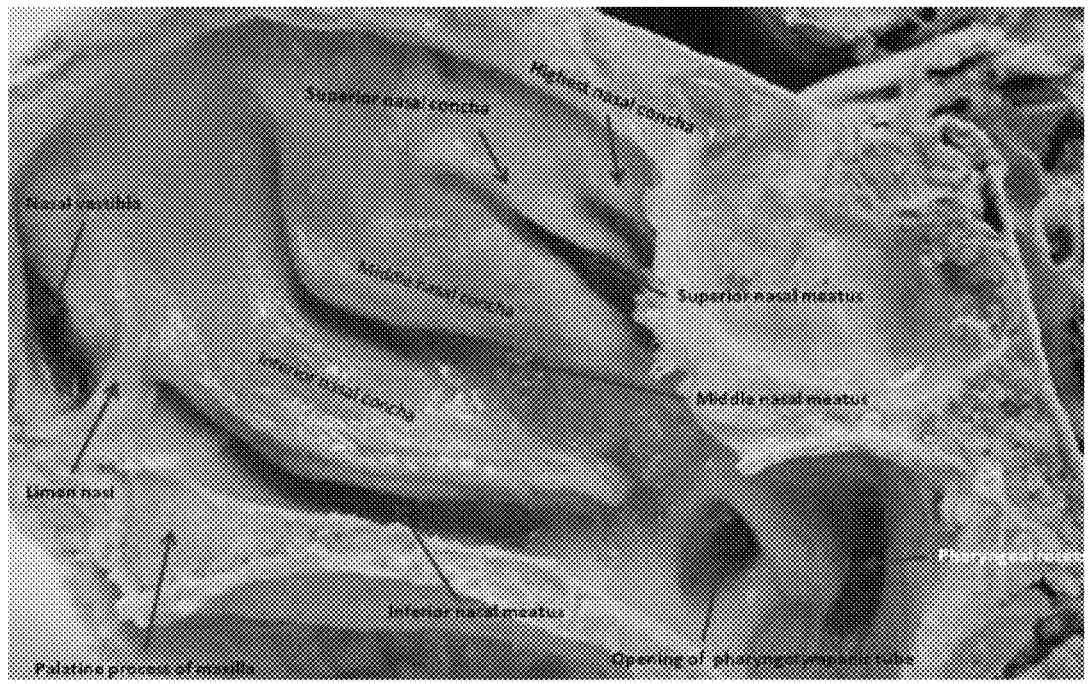
FIG. 2 illustrates how the inferior meatus directly drains in the lacrimal conduit.

Physiology of nasal secretions and retronasal flow as a cough producer:

The flow of runny nose consists of several aspects, the glands and goblet cells of the own mucosa of the septum and the wings of the nose, where erectil tissue of the turbinates explain both, congestion and vascular permeation with liquid output into the nasal light. The same process is in fact from the mucosa of the paranasal sinuses which secretions reaches the nose by draining to nose openings called meatus located, one below the middle turbinate called meatus medium containing other semilunar hiatus (other small openings to nasal light). In the lower hiatus, lead: The frontal sinus, the anterior ethmoid cells and the maxillary sinus, drain at the semilunar hiatus top, where the discharge ends from the rest of the anterior ethmoidal cells. The superior meatus between the superior conchae and the medium turbinate is where secrtetions flow from the sphenoid sinus and posterior ethmoid cells. Since this meatus is the most posterior, the discharge from it, could flow more easily into the nasopharynx and causing cough. The inferior meatus directly drains in the lacrimal conduit (FIG. 2).

All this secretions and liquid discharge, does not necessarily go to the front of the nose, as runny nose, but on many occasions it does to the back part of the nose, perhaps according to the meatus which drains and related to the actual position of the individual (supine position facilitates drainage back), causing both, hoarseness and cough.

In children, on the other hand, the ratio between the size of the drainage holes (meatus) and the nasal light is greater than the said ratio (meatus and sinuses) in adults then, some signs and symptoms of rhinosinusitis and colds are different in those age groups because the child produces and eliminates proportionally more secretions mainly through the posterior part of the nose, which in turn may causes more cough than in adults.

Basic parasympathetic nasal physiology, muscarinic and ipratropium bromide: Anticholinergic drugs have utility inter alia, to regulate glandular secretion in allergic rhinitis and sinusitis. The cholinergic reflexes are the most potent in activating exocytosis from submucosal glands respectively in both, lower and upper airways.

The acetylcholine action on postganglionic neurons, regulate specific muscarinic receptors subtypes, located on smooth muscle and submucosa airways glands. 4 receptor types have been defined as $M_1$, $M_2$, $M_3$ and $M_4$, Vagal efferent preganglion fibers that produce acetylcholine, originate from tenth dorsal nucleus in brainstem and parasympathetic ganglia innervate larynx and tracheobronchial tree. Innervation of nasal cavity, etmoidal sinuses and posterior parasympathetic, come from preganglion of the seventh pair (facial), originated from the salivary nucleus and passes through the Vidian channel to synapse in sphenepalatine ganglion motor fibers. The postganglionic cholinergic fibers innervate glands in the nasal, pharyngeal and traqueobronchial tree mucosa[33].

The parasimpathetic brainstem nucleus is capable of inducing independent efferent responses in nose, larynx and tracheobronchial tree.

Submucosal glands are densely innervated. Atropine blocks essentially all secretory glands and only partially blocking the blood flow neurogenically induced[34-35].

Autoradiographic uptake studies indicate that muscarininc receptors are located in submucosal glands, parasympathetic ganglia and nerve branches[36,37]. In the nasal mucosa, $M_1$ and $M_3$ receptors are found in the glands and lower levels in cells endoteiiaies arterioles, in arterio-venous anastomoses, capacitance vessels and venous sinusoids.[37,38] $M_3$ receptors predominate in a 2:1 ratio.

Agonists and antagonists now available do not have sufficient selectivity to discriminate between receptor subtypes. M3 receptors regulate glandular secretion and bronchoconstriction in the human respiratory tract[38,39].

$M_3$ receptors sites and m3mRna gene are distributed through large and small airways, they are found in large concentrations in submucosal glands in which produce exocytosis. $M_3$ receptors are expressed in lower densities in the nasal epithelium and endotelium where it is thought, contribute to the goblett cells secretion, ion and water transport, and vasodilatation[40,41].

Atropine and ipratropium bromide are antagonists that inhibit cholinergic glandular secretion and bronchoconstriction, mediated by $M_3$ receptors. Selective antagonists of $M_3$, such as Darifenacin (UK-88.525) and Revatropate (UK-112.126), may offer advantages while block receptor during glandular exocytosis without interferin inhibitory mechanisms of $M_2$ autorreceptors[42].

In vivo colinergic reflexes act on resistance vessels to increase the blood flow in the nasal surface, but has a limited effect on capacitance vessels (to fill nasal sinusoids leading nasal congestion) controlling mucosal thickness or on venules, that are the site of vascular permeability[34,43]. $M_3$ receptors can participate in a limited way in nasal vasodilator reflexes[38]. Even if small amounts of plasma proteins such as albumin and IgG are released in response to metacolin (parasympathomimetic drug), it does not contribute significantly to the production of secretion. These macromolecules should:

1. —Enter glandular and acinar ducts from the interstitium by diffusion between the cells gap and are expelled along with the large macromolecules in mucus.

2. —Deposited from post-capilarie venules, after activation of $M_3$ receptors in endotelial cells, or 3. —Go out by fenestrated capillaries when the vasodilator effect increases blood pressure transmitted to those previously permeabilized vessels.

Stimulation of nasal nociceptive sensory innervation by cold air, capsaicin, histamine, bradykinin, triggers allergic reactions or parasympathetic reflexes[10,33,38]. These reflexes are the most important mechanisms in regulate secretion by exocytosis of serous and mucous glands, a finding which has been clearly demonstrated in unilateral nasal provocation models. For example with histamine unilateral challenge, $H_1$ receptors vessels are stimulated then stimulate vasodilation with sinusoidal filling with blood, leading obstruction of nasal airflow, and increasing permeability with albumin and IgG enriched fluid secretion, it stimulate other tingling sensations that trigger protective reflexes including sneezing. They also triggered bilateral cholinergic reflexes that stimulate glandular secretion of mucoglicoproteins from mucosal cells, lysozyme from serous cells, lactoferrine, secretory IgA and other non-specific antimicrobial factors. The non cholinergic nasal obstruction mediated reflex component has not been quantified.

Muscarinic antagonist such as atropine and ipratropium bromide effectively reduce glandular secretion and "dry" the mucosa, but have no effect on sneezing or vascular nasal congestion[10]. Selective antagonist receptors may have clinical utility in rhinitis, where glandular parasympathetic secretion is an important cause of patient discomfort. However, significant reductions in the volume of glandular secretion can reduce the amounts of antimicrobial and lubricants proteins derived from serous cells on the mucosal surface and may produce dryness, irritation and nerve stimulation.

With respect to the basic physiology sympathetic agonistic action, a receptors and sympathomimetic drugs such as oximetazoline, venules and veins of nasal mucosa, they are innervated predominantly by sympathetic nerves. However, the arteries that supply the glands are innervated by parasympathetic and adrenergic nerves. Cholinergic stimulation (parasympathetic) dilates arterioles, thereby increasing blood flow to the glands, mucous and serous cells with subsequent secretion of proteins and other substances.

It was demonstrated that α-2 receptors act preferentially on venular ends and α-1 receptors constricts arteries[44]. It is interesting to note that the topical decongestant oximetazoline, an agonist with high affinity for α-1 and α-2 receptors, produces a dose dependent contraction, with inhibiting effect with α-1 antagonist receptor (prazosin) and minimal inhibitory effect with an α-2 receptor antagonist (yohimbine).

It has been suggested that α-2 agonists predominate in venous sinusoids and congestion regulation[45]. When blood flow decreases through microvasculature and through glands also decrease both, plasma exudation and glandular secretion[46].

Alpha-adrenoceptors are cell membrane receptors which belong to 7 transmembrane links associated receptor of G protein family. Six genes for α-adrenoceptors have been identified and sequenced[47].

The α-1 adrenoceptors are coupled via $G_{q/11}$ to C-phospholipase, and receptor activation results in the production of inositol triphosphate (IP3) and diacyl-glycerol, thus an increase in $Ca^{2+}$ with activation of protein kinases such as Protein Kinase C (PKC).[48] The α-2-adrenoceptors are negatively coupled via $G\ i_{/o}$ to adenilciciase to decrease cyclic AMP. Activation of α-2 adrenoceptors Q2A causes release inhibition of neurotransmisors. Nasal obstruction associated with acute rhinitis, is probably due to increase of vascular permeability as a result of dilation of the corpus cavernosum and mucosal congestion.

The mucosal of the nasal septum and the lateral tissue of the middle turbinate are intensely vascularized. In the surface of nasal mucosa, blood flows at a rate of 40 mL/100 g tissue per minute[49].

The mucosal tissue shrinks when exposed to sympathomimetic vasoconstrictor decongestant such as the standard topical oximetazoline. The vascular smooth muscle of the nasal mucosa is believed to be the only tissue where has that contractility[69]. Previous studies have shown that α-adrenoceptors are distributed in dogs[46], pigs[51] and humans[44,52], in the nasal mucosa and the α-2 adrenoceptors mediate vasoconstriction in the nasal mucosa of pigs and humans. The links-radioligands studies using antagonists to $α_1$-adrenoceptors ($^{13}$ H) prazosin and the $α_2$-adrenoceptor antagonist [3H] rawolscina, have demonstrated in humans the expression of both proteins adrenoceptors $α_2^-$ and $α_1^{-53}$. However these radioligands can not discriminate between adrenoceptor subtypes.

With respect to the oximetazolne and xilometazoline vasoconstriction, the receptor subtypes involved are unknown. That's why noradrenaline and adrenaline catecolamines are classified as imidazolines α-adrenoceptor non-selective agonists[44]. Only oximetazoline had been shown to induce responses $Ca^{2+}$ in heterologous cells expressing human $α_{1A}$-adrenoceptors[54].

Controversially, studies indicate that the α-adrenergic stimulation by imidazoles does not decrease, but increase the nasal glandular secretion[55].

Finally, as a rule, the two catecholamines, norepinephrine and epinephrine, show lower affinities compared to the imidazoles oximetazoline and xylometazoline[56]. The oximetazoline can produce a significant increase in blood pressure, fortunately only does it with large doses of 0.3% and no at standard doses of 0.01 to 0.1%[56].

Interactions between sympathetic and parasympathetic systems are not fully known so far, it is known that functionally there is a complex direct interaction between parasympathetic and sympathetic nervous systems, which is of significant importance. This interaction may explain the phenomenon on the other hand has been considered a puzzle.

On the one hand sympathetic relationship of noradrenaline released by nerve endings escapes into the blood or into the interstitial fluid, the remainder is inactivated while is received in α-adrenergic postsynapses effector sites, on target tissues. In fact, when a tissue is exposed to an α-adrenergic-blocker, results in a kind of noradrenaline overflow, which remains active for longer, and may affect other tissues.

The noradrenaline released suggests itself, that its physiological agonist effect exerts an inhibition to release noradrenaline from adrenergic nerve endings, in a inhibitory feedback functional character type, mediated by adrenergic receptors.

Thus, it explained that with various drugs that affect these receptors, different responses are obtained with respect to the release of the noradrenaline neurotransmiter:

α-adrenergic blockers - - - Increases noradrenaline flow
α-adrenergic agonists - - - Decreases norepinephrine flow The preceding shows the role of the direct inhibitory action of the sympathetic nervous system, at least on some of its effectors.[57] Dually innervated organs (like turbinate nasal mucosa) show a more complex relationship, as sympathetic can inhibit itself by negative feedback. The relationship between sympathetic, through its neurotransmitter noradrenaline and the parasimpathetic nerve endings, which are abundant in the capacitance vasculature and nasal sub-mucosal glands, is remarkable.

A research carried out some years ago[58], studied the effects of sympathomimetic catecolamines in parasympathetic transmission. What was found was a notable capacity of sympathomimetics, noradrenaline and adrenaline, to reduce the acetilcoline (parasympathetic) release from ileum guinea pigs nerve tissue. Noradrenaline reduced acetilcoline discharge in an average 56.8% (20 to 70%) while increasing concentrations of noradrenaline.

Regarding the oxymeiazoline effects on parasimpathetic system, Starke studied the effect of another sympathetic agent, the oxymetazoline, with relation to the parasympathetic transmission, finding that oximetazoline significantly inhibited the cardiac response of rabbit vagal electrical stimulation. Parasympathetic transmission was inhibited with decrease in the release of acetilcoline preganglionic and postganglionic nerve endings. In that study, oxymetazoline increased the range of heart beats that had previously decreased during the exposure to acetilcoline. When oxymetazoline infusion was stopped, this effect was rapidly and completely reversed[59].

Referring to the foregoing, it is apparent that if this happens in other tissues, particularly those with dual innervation, both sympathetic and parasympathetic, as in the nasal mucosa, may oxymetazoline acting on two different vias, when is topically administered:

1. Reducing congestion of the capacitance of the blood vessels due to its adrenergic effect on vascular smooth muscle which in turn could reduce permeability of these vessels that were already increased, for example because of a common cold.

2. Reducing the parasympathetic effect on nasal respiratory mucosa vessels and glands near them.

In relation to imidazoline derivatives, some results have been controversial, an example shows a study in which the xilometazoline decreased rhinorrhea (allegedly decrease in the permeability), even if it did belatedly, till 5 to 10 days of initiate the infectious process ($p<0.05$)[6]. Unlike the findings of another study, in which no dicreasesin rhinorrhea was found, on the contrary, increases with the use of xilometazoline when measured on day 1 of administration[2,49]. An alternative explanation is that these drugs may more active in reducing the permeability, when it has been previously increased by the action of inflammatory substances such as bradykinin[80], when which are released lately in the course of a viral infection.

Related to this type of infection, also mast cells release histamine locally (perhaps in an earlier phase than the release of bradykinin), which also has an important role in modulating rhinorrhea, possibly via interactions of sympathetic/parasympathetic systems, or acting directly on the mucous glands goblet cells and on blood vessels.

Finally, a knowledge that is relevant to the efficacy of the combination of Oxymetazoline and Ipratropium, is that the affinity of oxymetazoline to α-adrenergic receptors exceeds significantly that affinity for these receptors by noradrenaline[56]. This increased affinity may cause greater overflow of noradrenaline in tissues, and if this increased overflow (if it is greater) could affect differently, given above, the inhibition of both the sympathetic and parasympathetic fibers in some organs that, as the nose, are doubly innervated.[61] This greater affinity for receptors can result in reduced mucus secretion both, glandular (less parasympathetic effect) and that produced by variations in vascular permeability (less sympathetic effect).

There are some studies where was measured the nasal secretion amount of secretion, not cough, with drugs used. Next, a representative collection of some of them:

Graff[89] and Eccles[2] mentioned, using xilometazoline alone, and using ipratropium bromide alone, and the combination of oximetazolina and ipratropium bromide, found that the combination, after day 1 of treatment, there was a clear separation between nasal symptom scores fluid for placebo and ipratropium in the treated group. The differences were statistically significant compared to placebo ($p<0.0001$).

Eccles in 2008[6], using just xilometazoline: mentioned decreased nasal secretion compared with placebo, statistically significant $p<0.05$.

Kim[1], Hayden[62], Diamond[63] Dockhorn[64] in four different studies, using ipratropium alone, intranasally, found lower nasal discharge.

Evaluation of the Effectiveness of the Combination Oximetazoline and Ipratropium Bromide, Intranasaly, for the Treatment of Cough in Order to Elaborate the Patent Request:

An open pilot study with 6 patients with acute cough associated with common cold, using ipratropium bromide and oximetazoline combination intranasally, administered every 12 hours for 5 days. Patients were 3 to 54 years. Pediatric presentation was used in those of 3 to 12 years hereinafter use the adult presentation. All patients started coughing from 24 to 72 hours before they were enrolled, with clear predominance presenting at night and morning.

Cough was specifically evaluated by the method of 0 to 5 (0=no cough; 5=incapacitating cough) using graphics of cough presentation during the day and night, according to Dr. Hsu[86] and previously by Archer[88] (FIGS. 3 and 4). Results obtained showed significant decrease in coughing, both during the day and overnight, with greatest effect on the latter.

During the day, before intranasal administration of the combination drops, from an initial intensity of cough with an average score of 3.0 (frequent cough, which does not interfere with school or other activities), went down to score 1.6 (cough in one or two short periods) the first day and by 1.3 in the second day and finally to an intensity of 0.8 cough (without cough in virtually all patients) on day 5.

Figure 5:
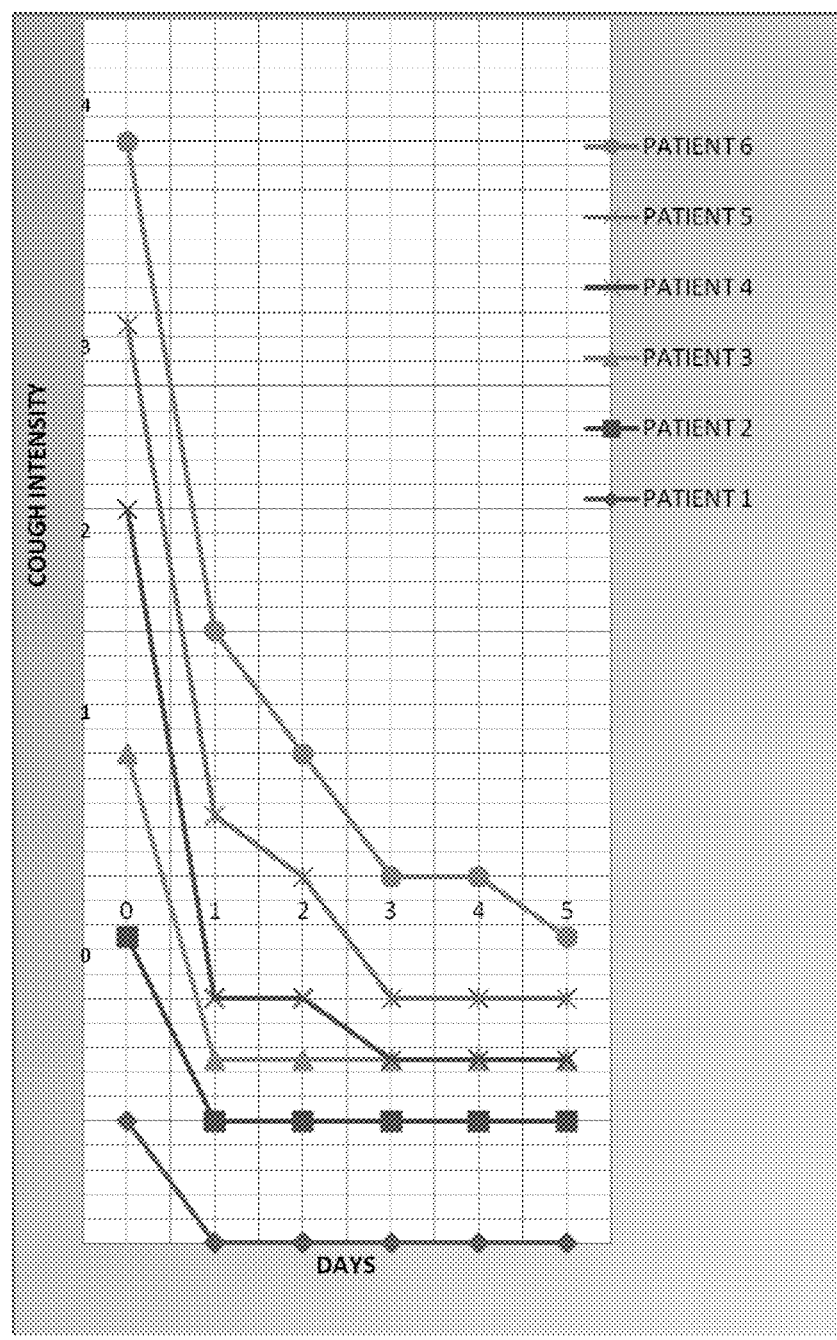
FIG. 5 illustrates a graph displaying the cough intensity of a patient during the day following administration of the composition.
Figure 6:
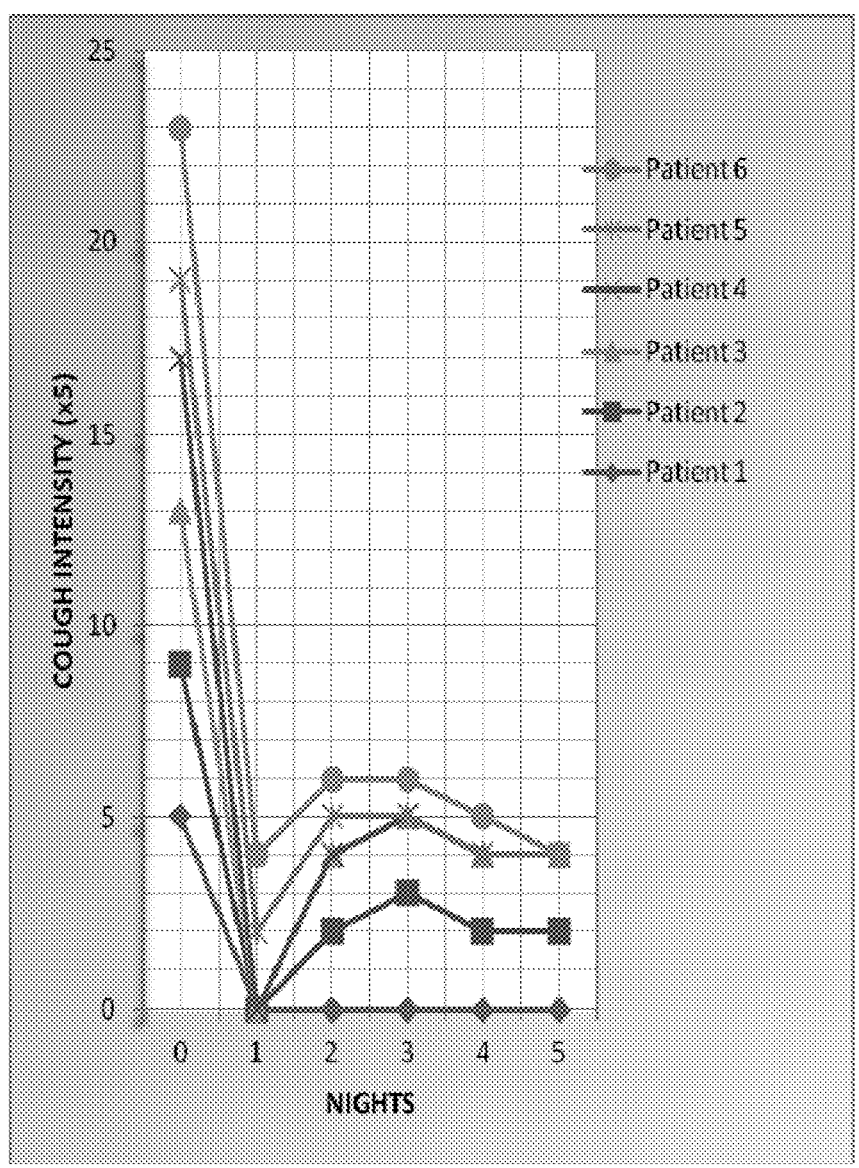
FIG. 6 illustrates a graph displaying the cough intensity of a patient during the day following administration of the composition.

At night, the effect was much more pronounced, starting before treatment with an intensity average cough of 3.8 (frequent cough that in most of patients were most of the night), fell during the combination management in the first night to an average intensity of 0.8, that is, practically disappeared nighttime cough, in a strongest effect showed in this pilot study in all patients evaluated (FIGS. 5 and 6).

At present, the research protocol called "Evaluation of the efficacy of the combination of oxymetazoline and ipratropium in nasal topical application for the treatment of cough associated with common cold" is underway, with a sample of 70 patients of 6 and 6 years. 12 years of age, with a double blind design and controlled by placebo, using the same cough measurement system (FIGS. 5 and 6)[65,66].

In summary, the racionale is the following: if in several studies a lower anterior nasal discharge has been demonstrated with the topical use of both drugs, both separately and in combination, it can be assumed that, when said secretion is directed backwards, towards the retronasal region and subsequently retropharyngeal, this decrease leads to a decrease in cough caused by this secretion.

REFERENCES

1.—kerlund A, Klint T, Olen L, Rundcrantz H. Nasal decongestant effect of oxymetazoline in the common cold: an objective dose-response study in 106 patients. J Laringol Otol 1989: 03 (8): 743-746.

2.—Eccles R, Pedersen A, Regberg D, Tulen to H, Borum P. Stjarne P. Efficacy and safety of topical combinations of ipratropium and xylometazoline for the treatment of symptoms of runny nose and nasal congestion associated with acute upper respiratory tract infection. Am J Rhinol 2007: 21 (1): 40-45, 3.—A Pitkáranta, M T Wecker, D C Korts, F G Hayden. Combined intranasal ipratropium bromide and oxymetazoiine in experimental rhinovirus infection. American Journal of Rhinology 1998; 12 (2): 125-9. DOI: 10.2500/105065898781390316.

4.—Pritchard S, Glover M, Guthrie G, Brum J, Ramsey D, Kappler G, Thomas P, S Stuart, Hull D, Gowland P. Effectiveness of 0.05% oxymetazoiine (Vicks Sinex Micromist®) nasal spray in the Treatment of objective nasal demonstrated congestion demonstrates to 12 h post-administration by magnetic resonance imaging. Pulm Pharmacol Ther. 2013. Pit: SI 084-5539 (13) 00187-3 doi: 10.1016/j.pupt.2013,08.002.

5.—O'Donell S R, Sympathomimetic vasoconstrictor as nasal descongestants. 1995 Austr Med J 62: 264-287.

6.—Eccles R, Eriksson M, Garreffa S, S C Chen S C. The nasal descongestant effect of xiiometazoline in the common cold. Am J Rhinol 15 2008. 22, 491-496.

7.—Stokes G M, Milner A D, Hodges I G C, Henry R L. Nebulised ipratropium bromide in wheezy infants and young children. Eur J Respir Dis 983; 64 (Suppl 28): 494-498.

8.—Stokes G M, Milner A D, Hodges I G C, Henry R L, Elphick M C. Nebulised therapy in acute severe bronchioiitis in infancy. Arch Dis Child 1983, 58: 279-283.

9.—Moayyedi P, et al Comparison of nebulised salbutamol alone and with ipratropium bromide in the pulmonary treatment of chronic obstructive disease. Thorax 1995; 50: 834837, 10. Mygind N, Borum P. Anticholinergic treatment of watery rhinorrhea. Am J Rhinol 1990; 4:1.

11.—Kim K T, Kerwin E, Landwehr L, Bernstein J A, Bruner D, Harris D, Drda K. On behalf of the Pediatric Atrovent Nasal Spray Study Group. Use of 0.06% nasal bromide ipratropium 25 spray in children aged 2 to 5 years due to Rhinorrhea With a common Cold or allergies. Ann Allergy Asthma Immunol. 2005; 94: 73-79
12.—Pratter M R. Chronic upper airway syndrome secondary to rhinosinus cough diseases (previously referred to as postnasal drip syndrome) ACCP Evidence based clinical practice guidelines. Chest 2006; 129: 633-71 S.
13.—Schroeder K, Fahey T. Over-the-counter medications for acute cough in children and adults in ambulatory settings. Cochrane Database Syst Rev. 30 18 Oct. 2004; (4): CD001831
14.—Simaserk M, Biandino D A. Treatment of the common Cold. Am Farn Physician 2007; 75; 515-20
15.—Paul I M, Yoder K E, Crowell K R, Shaffer M L, McMillan H S, Carlson L C et al. Effect of dextromethorphan, diphenhyramine and placebo on nocturnal cough and sleep for coughing quality children and their parents. Pediatrias 2004: 1 14: E85-90.
16.—Brodie M, Graham C, McKean M. Childhood cough. BMJ 2012; 344: 40-45.
17.—Shields M D, Bush A, Everard M L, McKenzie S, R Primhak, on behalf of the British Thoracic Society Cough Guideline Group. Recommendations for the assessment and management of cough in children. Thorax 2008; 83 (Suppl III)iii1-iii15.
18.—Sung S, Cranswick N. A Cochrane review in 2008 found the treatments were not more effective than placebo for acute cough in children. The review included two trials with antitussives, with two antihistamines, decongestants and one trial with antitussive/bronchodilator combinations. Prescr Aust 2009; 32: 122-4.
19.—Dealleaume L, Tweed B, Neher J O. Do OTC cough remedies relief in acute URIs? J Fam Pract 2009 October; S8 (10): 559a-c.
20.—Bell E A, Tunkel D E. Over-the-counter cough medications in children: Are they helpful? Otolaryngol Head Neck Surg. 2010 May; 142 (5): 647-50 doi: 10.1016/j.otolaringol head neck Surg 2010 May:142(5):647-50. Doi. 1016/j.otohns.2010.01.019.
21.—Shefrin A E, Goldman R D. Use of over-the-counter cough medications and cold in children. Can Fam Physician. 2009 November; 55 (11): 1081-3.
22.—Kelley L K, Alien P J. Managing acute cough in children: evidence-based guidelines. Pediatr Nurs. November-December 2007: 33 (6): 515-24.
23.—Carr B C. Efficacy, abuse, and toxicity of over-the counter cough and cold medicines in the pediatric population. Curr Opin Pediatr 50, 2006 April; 18 (2): 184-8
24.—Chang A B, Peake J, McEirea M S, Anti-histamines prolonged for non-specific cough in children. Cochrane Database Syst Rev. 2008 Apr. 16; (2): CD005604, doi: 10.1002/14S51858, CD005604.pub3.
25.—Arroll B. No antibiotic treatments for upper-respiratory tract infections (common Cold). Respir Med. 2005 December; 99 (12): 1477-1484.
26.—Wang, Bettiol S, Thompson M J, Roberts N W, Perera R, Heneghan C J, Hamden A. Symptomatic treatment of the cough in whooping cough. Cochrane Database Syst Rev. 2014 Sep. 22; 9: CD003257. doi:
27.—Chang C C, Cheng A C. Chang A B. Over-the-counter (OTC) medications to reduce cough as adjunt to antibiotics for acute pneumonia in children and adults. Published Online: 10 Mar. 2014 Assessed as up-to-date: 22 Jan. 2014 Doi: 10.1002/14851858.CD006088, pub4,
28.—Courley F J, Irwin R S, Pratter M R, Stivers D H, Doern G V, Vernaglia P A, Larkin A B, Baker S P. Cough in the common cold. Am Rev Resp Dis 1988; 138: 305-311.
29.—The Japanese Respiratory Society. The committee for the Society Respiratory Japanese guidelines for management of cough. Cough in specific populations (pediatric Patients, elderly patients and Patients With underlying disease). Respirology (2006) 1 (Suppl. 4 S175-S186).
30. Graf P, Eccles R, Chen S. Efficacy and safety of intranasal xilometazoline and ipratropium in Patients with common cold. Expert Opin Pharmacother. (2009) 10 (5): 889-908.
31.—Chung K F, Lalloo U G. Diagnosis and management of chronic persistent dry cough. Postgrad Med J 1998; 72: 594-598,
32.—Uddman R, Sundler F, Innervation of the upper airways. Clin Chest Med 1986; 7: 201.
33.—Baraniuk J N. Neural Control of human nasal secretion. Pulm Pharmacol 1991; 4: 20.
34.—Lundberg J M, Angaard A, Fahrenkrug J. Complementary role of vasoactive intestinal peptide (VIP) and acetylcoline for submandibular gland blood flow and secretion. Acta Physiol Scand 1981: 113: 329-23
35.—Stijarne P, J S Lacroix, Angaard A, Lundberg J M. Compartment analysis of vascular effects of neuropeptides and Capsaicin in the pig nasal mucosa. Acta Physiol Scand 1991: 141: 335
36.—Barnes P J, Nadel J A, Roberts J M, Basbaum C B: Muscarinic receptor subtypes in human lung and trachea: Autoradiographic localization using $^{[3H]}$ quinuclidinyl benzilate. Eur J Pharmacol 1983: 86: 103
37.—Okayama, Baraniuk J N, Merida M, Kaliner M A. Autoradiographic localization of muscarinic receptor subtypes in human nasal mucosa 30. J Allergy Clin Immunol 1992; 89: 1144.
38.—Baraniuk J N, Kaliner M A, Barnes P J, Muscarinic $M_3$ receptors mRNA in situ Hybridization in human nasal mucosa. Am J Rhinol 1992; 6:145.
39.—Eglen R M, Reddy H, Watson Ni, Challis RAI. Muscarinic receptor subtypes in smoothmuscle acetylcholine. TiPS 1994; 15:114.
40.—McCormack D G, Mak J C, Minette P, Barnes P J. Muscarinic receptor subtypes mediating vasodilation in the pulmonary artery. Eur J Pharmacol 1993; 158: 293.
41.—Tokuyama K, Kuo H P, Rohode JAL, Barnes P J, Rogers D F. Neural Control of goblet cell secretion in guinea pig airways. Am J Physiol (Lung Cell Mol Physiol) 1990; 259: L108.
42.—Alabaster V A. Discovery and development of selective $M_3$ antagonists for clinical use. Life Sci 1997: 60: 1053-1060. 40 43.—
43.—Raphael G R, Baraniuk J N, Kauner M A. How and why the nose runs. J Immunol 1991 Allergy Cun; 87: 457.
44.—Corboz M R, Varty L M, Rizzo C A, et al. Pharmacological characterization of a2-adrenoceptor-mediated responses in pig nasal mucosa. Auton, Autacoid Pharmacol 2003; 23: 208-219.
45.—T L Berridge, Roach A G. Characterization α-adrenoceptors of the vasculature in the mucosa of the nasal canine. Br Pharmacol 1986; 88: 345-354.
46.—O'Donell S R. Sympathomimetic vasoconstrictors as nasal descongestants Med J Aust. 1995 62: 264-267.
47. Bylund D B, Bond R A, Clarke D E, Et al. Adrenoceptors. The IUPHAR Compendium of receptor characterization and classification. IUPHAR Media. London U K, 1998:58-74.
48.—Docherty J R. Subtypes of functional alpha1 and alpha$_2$ EUR J Pharm Ichimuramacol adrenoceptors. 1998: 361: 1-15

49.—Drucs H M, R F Bonner, Patow C, Choo Q, Kaliner M A. Response of nasal blood flow to neurohormones as laser-Doppler Measured by velocimetry. J Appl Phisiol. 984; 57: 1276-1283. S G.-lchimura K, Jackson R T, alpha2-adrenoceptors Evidence heard in the nasal blood vessels of the dog. Arch Otolaryngol. 5 1984 110: 647-651.

51.—Corboz M R, Riveli M A, Varty L. Muíter J B Cartwhrigt M D, Rizzo ChA, Eckel S P, Anthes J C, Hey J A. Pharmacological characterization of postjunctional α-adrenoceptors in human nasal mucosa. Am J Rhinol. 2005, 19: 495-502.

52—Anderson K E, Bende M. Adrenoceptors in the Control of human nasal mucous membrane blood flow. Annal Otol Rhino laryngol 1984; 88: 345-354.

53.—Van Megen Y J B, K! Aassen A B M, Rodriguez de Miranda J F, Van Gunneken C A M, Wentges B T R. Alterations of adrenoceptors in the nasal mucosa of allergic Patients in Comparison with non-alleric individuals. J Clin Allergy Immunol 1991: 87: 530-540.

54.—Hone K, Obiika, Foglar R, G. Tsuimoto. Selectivity of the α-adrenoceptors imidazoline agonist (oxymetazoline and cirazoline) for human cloned a1-adrenoceptors subtypes. Br J Pharmacol. 1995: 118: 1611-1618.

55.—Maim L. Vascular and secretory effect of adrenoceptor agonists and peptides in the nose. Eur Respir Dis 19883; 64 (sup 128): 139-142.

56. B-Haenich, Walstab J, Herberhold S, Bootz F, Tschaikin, R. Ramserger Bónisch. Alpha-adrenoceptor agonistic activity of oximetazoline and xilometazolne. 2009 Societé Sociate Francaise de Pharmacologie et de Thérapeutique de Fundamental & Clinical Pharmacology. 24: 729-739. 20

57.—Jansson G, artinson J. Studies on the ganglionic site of action of sympathetic outflow to the Stomach. 1986 Acta Physiol Scand 69, 184-192

58.—Patón W D, Vizi E S. The inhibitory action of noradrenaline and adrenaline on acetylcholine output by guinea-pig ileum longitudinal muscle strip. Br J Pharmacol 969; 35: 10-28.

59.—Starke K. Alpha sympathomimetic inhibition of adrenergic and cholinergic transmission in the rabbit heart. 1972 274 Arch Pharmacol 25: 18-45.

60.—Proud D, Reynolds C J, Lacapra S, Kagey-Sobolka A, Lichtenstein L M, Naclerio R M. Nasal provocation with bradykinin induces symptoms rhinitis and sore throat. Am Rev Resp Dis 1988; 137: 613-616.

61.—Mujic M, Van Rossurn J M: Comparative pharmacodiynamics of sympathomimetic imidazolines; studies on intestinal smooth muscle of the rabbit and the cardiovascular system of the cat. Arch int Pharmacodyn 1985. 155: 432-449.

62.—Hayden F G, Diamond L, Wood P B, et al. Effectiveness and safety of intranasa! ipratropium bromide in common colds. A randomized, double blind, placebo controlled trial, Ann Intern Med 1996; 125: 89-97.

63.—Diamond L, Dockhorn R J, Kisicki J C, et al. A dose-response study of the safety and efficacy of ipratropium bromide nasal spray in the treatment of the common Cold. J Allergy clin Immunol 1995; 95: 1139-46.

64.—Dockhorn R J, Grossman J, Posner M, et al. A double blind, placebo controlled study of a safety and efficacy of ipratropium bromide nasal spray versus placebo in patients with common cold. J Allergy clin Immunol. 1992; 90:1076-1082.

65. Archer L N, Simpson H. Night counts cough and diary-card scores in asthma; Arch Dis Chiid 1985; 60: 473-474.

66.—Hsu J Y, Stone R A, Logan-Sinclair R B, C M Bussi, Chung K F. Coughing in Patients with Frequency persistent cough: assessment using 24 hour ambulatory recorder. Eur Respir J. 1994, 7, 1246-1253).

The invention claimed is:

1. A pharmaceutical composition for treatment for a cough caused by a posterior nasal secretion, comprising ipratropium bromide or a pharmaceutically acceptable salt and oxymetazoline hydrochloride or a pharmaceutically acceptable salt, for the preparation of an intranasal drug;
    wherein the treatment is formulated in the form of an aqueous solution comprising Ipratropium bromide in dilutions of 105.0, 52.5 and 21.0 mg/100 mL, and oxymetazoline hydrochloride in dilutions of 50.0, 25.0 and 10.0 mg/100 mL, for adult, children, and pediatric respectively.

2. The pharmaceutical composition of claim 1, further comprising disodium EDTA (disodium ethylenediaminetetraacetate) as a stabilizer present in concentration of 50.0 mg/100 mL.

3. The pharmaceutical composition of claim 1, further comprising benzalkonium chloride as a preservative present in a concentration of 10.0 mg/100 mL.

4. The pharmaceutical composition of claim 1, further comprising 0.1N hydrochloric acid and 0.1N sodium hydroxide pH stabilizing agents in sufficient quantities to adjust the pH of the treatment to 4.75.

5. The pharmaceutical composition of to claim 1, further comprising a humectant in the form of glycerin at a concentration of 5000.0 mg/100 mL.

6. The pharmaceutical composition of claim 1, further comprising potassium monobasic phosphate at a concentration of 68.04 mg/100 mL to act as a stabilizer.

7. The pharmaceutical composition of claim 1, wherein the treatment is adapted to be administered intransally.

8. The pharmaceutical composition of claim 1, wherein the treatment is administered in the form selected from the group consisting of: droplets, microdroplets, aerosol, pressurized aerosol, metered dose pressurized aerosol, spray, microspray, atomization, nasal breeze, or by soft mist inhaler methods, or microdifussion nozzles.

* * * * *